United States Patent
Lyngstadaas et al.

(10) Patent No.: US 6,979,670 B1
(45) Date of Patent: Dec. 27, 2005

(54) MATRIX PROTEIN COMPOSITIONS FOR GRAFTING

(75) Inventors: Ståle Petter Lyngstadaas, Nesoddtangen (NO); STina Gestrelius, Lund (SE)

(73) Assignee: Biora BioEx AB, Malmo (SE)

( * ) Notice: Subject to any disclaimer, the term of this patent is extended or adjusted under 35 U.S.C. 154(b) by 0 days.

(21) Appl. No.: 09/521,907

(22) Filed: Mar. 9, 2000

Related U.S. Application Data (60) Provisional application No. 60/134,954, filed on May 19, 1999.

(30) Foreign Application Priority Data

Mar. 10, 1999 (DK) ............................... 1999 00337

(51) Int. Cl.[7] ........................................... A61K 38/17
(52) U.S. Cl. ............................. 514/2; 424/549; 514/21
(58) Field of Search ............................ 424/278.1, 549; 514/1, 2, 12, 21

(56) References Cited

U.S. PATENT DOCUMENTS

| | | | |
|---|---|---|---|
| 4,672,032 A | | 6/1987 | Slavkin et al. |
| 6,022,862 A | * | 2/2000 | Haimes et al. |
| 2002/0169105 A1 | * | 11/2002 | Gestrelius et al. ............ 514/2 |

FOREIGN PATENT DOCUMENTS

| | | |
|---|---|---|
| SE | 0 263 086 A1 | 4/1988 |
| SE | 0 337 967 | 10/1989 |

OTHER PUBLICATIONS

Carlson-Mann et al. Probe p. 178 and 193 vol. 32, No. 5, 1998.*
Hammarstrom et al. J. Clin. Periodont. vol. 24 pp. 669-677, 1997.*
Palaiologou et al. J Periodont. vol. 72 pp. 798-807 Abstract only, 2001.*
Mellonig, James T., "Enamel Matrix Derivative for Periodontal Reconstructive Surgery: Technique and Clinical Histologic Case Report", The International Journal of Periodontics & Restorative Dentistry, vol. 19, No. 1, Feb. 1999, pp. 9-19.
W.H. Eaglestein and V. Falanga, Cutis 62 (1 Suppl.), Jul. 1998, p. 1-8. (Enclosed is a copy of this article taken from http://woundcarenet.com "Advances in Wound Care").
B. Rahfoth et al., Osteoarthritis Cartilage 6 (1), 1998, pp. 50-65.
C. Robinson, Eur. J. Oral Science, Jan. 1998, 106 Suppl. 1:282-91.
Fincham et al., J. Structural Biol., 1994, Mar.-Apr.; 112 (2):103-9.
Fincham et al., J. Structural Biol., 1995, Jul.-Aug.; 115(1): 50-9.
S. Sundell, Swed. Dent. J. 10(4), 1986, pp. 151-163.

* cited by examiner

*Primary Examiner*—David Saunders
(74) *Attorney, Agent, or Firm*—Kudirka & Jobse, LLP (57) ABSTRACT

Enamel matrix, enamel matrix derivatives and/or enamel matrix proteins are used in the preparation of a pharmaceutical composition for promoting the take of a graft, e.g. in soft tissue such as skin or mucosa or mineralized tissue such as bone.

23 Claims, 6 Drawing Sheets

MATRIX PROTEIN COMPOSITIONS FOR GRAFTING

This application claims the benefit of U.S. Provisional Application No. 60/134,954 filed on May 19, 1999.

FIELD OF THE INVENTION

The present invention relates to the uses of enamel matrix, enamel matrix derivatives and/or enamel matrix proteins or peptides as therapeutic or prophylactic agents in connection with grafting.

BACKGROUND OF THE INVENTION

Enamel matrix proteins such as those present in enamel matrix are most well-known as precursors to enamel. Enamel proteins and enamel matrix derivatives have previously been described in the patent literature to induce hard tissue formation (i.e. enamel formation, U.S. Pat. No. 4,672,032 (Slavkin)) or binding between hard tissues (EP-B-0 337 967 and EP-B-0 263 086). Thus, the prior art is solely centred on regeneration of hard tissues, while the present invention is concerned with beneficial effects on grafting or transplantation of soft and hard tissue.

SUMMARY OF THE INVENTION

The present invention is based on the finding that enamel matrix, enamel matrix derivatives and/or enamel matrix proteins (collectively termed "an active enamel substance" in the following) are beneficial agents for the enhancement or improvement of the attachment or healing of grafts. As demonstrated in the experimental section herein, the enamel matrix, enamel matrix derivatives and/or enamel matrix proteins exert especially useful effects in the healing of skin grafts.

Accordingly, the invention relates to the use of a preparation of an active enamel substance for the preparation of a pharmaceutical or cosmetic composition for promoting the take of a graft. It is anticipated that, in addition to the healing itself, the extent of scarring often accompanied with grafting procedures may be reduced by such use.

In another aspect, the present invention relates to a method of promoting the take of a graft, the method comprising administering to a mammal in need thereof a prophylactically or therapeutically effective amount of an active enamel substance.

In the present context, the term "take of a graft" is intended to indicate the entire healing process involved in the grafting procedure from the initial attachment of the graft to proliferation of fibroblasts, generation of granulation tissue, production of collagen by fibroblasts, and revascularisation, and, in case of surface grafts such as skin or mucosal grafts, keratinocyte migration into the graft bed. The term "mammal" is intended to indicate a member of any mammalian species which may advantageously be treated by the method of the invention, including domesticated mammals such as horses, cattle, pigs, dogs and cats, or, preferably, humans.

DETAILED DISCLOSURE OF THE INVENTION

Based on the present inventors' current findings, the active enamel substance is believed to be most beneficial for use in connection with grafts of non-mineralized tissue such as soft tissue comprising a substantial proportion of epithelial cells such as skin and mucosa. However, the active enamel substance may also be used successfully in connection with grafts of other tissue with high regenerative properties such as bone and cartilage, or even in connection with corneal transplants.

Skin and Mucosal Grafting

In dermatological surgery, grafts are most commonly used to repair lesions occurring after surgical excisions such as the removal of skin cancers, traumatic lesions, e.g. resulting from accidents, burns (whether thermal, chemical or electrical) or pathological processes, e.g. leg or foot ulcers.

Depending on the type of lesion to be repaired by grafting, e.g. whether it is a deep or more superficial lesion, and location of the lesion, e.g. whether the recipient (graft) bed comprises a sufficient vascular supply for capillary regrowth or whether the tissue at the recipient site is exposed bone, cartilage or tendon which does not contain a sufficient vascular supply, different types of graft will normally be applied. Thus, full-thickness skin grafts have traditionally been employed to repair facial lesions because such grafts often provide a more aesthetically pleasing result. "Full-thickness skin grafts" are intended to indicate grafts which are composed of both the epidermis and the entire thickness of the dermis, including structures such as hair follicles, sweat glands and nerves. Full-thickness skin grafts are therefore also preferred for use in connection with hair transplants. When performing full-thickness skin transplants, donor skin is excised from a suitable site and defatted (i.e. adipose tissue is removed from the graft). The recipient bed is cleaned with an antibacterial agent and rinsed. The graft is suitably trimmed to the size of the recipient site and placed dermis down on the recipient bed. The graft is then secured by suturing, and may be further immobilised by means of a suitable dressing or bandage. While full-thickness skin grafts tend to give the best results from an aesthetic point of view, graft take is often more difficult to obtain because revascularisation of the graft is required.

Another type of graft is the split-thickness skin graft which is composed of the entire thickness of the epidermis and a partial-thickness dermis. They have the advantage of containing less tissue for revascularisation and are more likely to be successful on various types of recipient bed than full-thickness grafts. Split-thickness skin grafts are often used to cover more extensive lesions but are often less aesthetically attractive than the full-thickness grafts. To cover large lesions such as extensive burns, split-thickness grafts may be used as seed or mesh grafts which means that the graft is divided into smaller portions (such as strips) and placed on the lesion. New epithelial growth then takes place from each of the portions of skin grafted onto the lesion.

More recently, at number of skin equivalents have been developed either from bioengineered epidermal cells, such as fibroblasts and keratinocytes, or from acellular dermal matrix. Examples of cultured epidermal cells include human fibroblasts (derived from neonatal foreskin) which is marketed by Novartis under the trade name Appligraf, and dermal tissue cells marketed by Smith & Nephew under the trade name Dermagraft and Dermagraft TC. Other examples include cultured keratinocyte grafts, cultured allogenic keratinocyte grafts, acellular collagen matrices and cellular matrices (as reviewed in, e.g. W H Eaglstein and V. Falanga, *Cutis* 62 (1 Suppl.), July 1998, pp. 1–8). An example of an acellular product is AlloDerm manufactured by LifeCell Corp.

Bone Grafts

Bone grafts may typically be applied to promote healing of complicated fractures. Various types of bone grafts are known, including autogenous fresh (living) cancellous and cortical bone, and demineralised bone matrix containing cells such as skeletal stem cells which, on stimulation with growth factors, differentiate into bone and cartilage. Such growth factors include, i.a., PDGF and TGF-β production of which has been observed to be stimulated in the presence of the active enamel substance. It is therefore anticipated that the inclusion of active enamel substance in such grafts or coadministration thereof during surgical procedures for the grafting of bone tissue may substantially promote the healing of the graft.

The use of active enamel substance mixed with demineralized, freeze-dried bone allograft has been suggested by JT Mellonig, *Int. J. Periodontics Restorative Dent.* 19, 1999, pp. 9–19, in connection with healing of bone lesions in the periodontium. This type of allograft is composed of dead tissue and merely acts as a carrier for the active enamel substance, whereas it does not participate actively in the bone tissue regeneration process.

According to the present invention it has surprisingly been found that the active enamel substance is capable of promoting the attachment and healing of a graft comprising living bone tissue or living cells capable of maturing into bone tissue. Furthermore, it has been found possible to use the active enamel substance which, in nature, is only found in the periodontal environment during tooth development for promoting graft attachment and healing of other types of bone tissue than alveolar bone or other mineralized tissue in the periodontium.

Cartilage Grafts

It has previously been disclosed (B Rahfoth et al., *Osteoarthritis Cartilage* 6 (1), 1998, pp. 50–65) that defects of articular cartilage in knees and other joints may be repaired by means of implants composed of chondrocytes embedded in a carrier matrix such as agarose. It is expected that the inclusion of active enamel substance in such implants may substantially stimulate the healing of the graft.

At sites of graft attachment there is an increased risk that the new tissue formed at the interface between the grafted tissue and the recipient bed is structurally and chemically unlike the original tissue (scar tissue). In the early stage of tissue repair, one process which is almost always involved is the formation of a transient connective tissue in the area of tissue injury. This process starts by forming a new extracellular collagen matrix by fibroblasts. This new extracellular collagen matrix is then the support for a connective tissue during the final healing process. The final healing is in most tissues a scar formation containing connective tissue. In tissues which have regenerative properties, such as skin and bone, the final healing includes regeneration of the original tissue. This regenerated tissue has frequently also some scar characteristics, e.g. a thickening of a healed bone fracture.

The stages of graft attachment and healing normally include inflammation (normally 1–3 days), migration (normally 1–6 days), proliferation (normally 3–24 days) and maturation (normally 1–12 months). The healing process is a complex and well orchestrated physiological process that involves migration, proliferation and differentiation of a variety of cell types as well as synthesis of matrix components. The healing process may be separated into the following phases:

i) Haemostasis and Inflammation

When platelets are present outside the circulatory system and exposed to thrombin and collagen, they become activated and they aggregate. Thus, platelets initiate the repair process by aggregating and forming a temporary plug to ensure haemostasis and prevent invasion from bacteria. The activated platelets initiate the coagulation system and release growth factors like platelet-derived growth factor (PDGF) and epidermal growth factors (EGFs) and transforming growth factors (TGFs).

The first cells to invade the site of a graft are neutrophils followed by monocytes which are activated by macrophages.

The major role of neutrophils appears to be clearing the recipient bed at the site of the graft of or defending the graft against contaminating bacteria and to improve the healing of the graft by removing dead cells and platelets. The infiltration of neutrophils ceases within about the first 48 hours provided that no bacterial contamination is present in the wound. Excess neutrophils are phagocytosed by tissue macrophages recruited from the circulating pool of blood-borne monocytes. Macrophages are believed to be essential for efficient wound healing in that they also are responsible for phagocytosis of pathogenic organisms and a clearing up of tissue debris. Furthermore, they release numerous factors involved in subsequent events of the healing process. The macrophages attract fibroblasts which start the production of collagen.

ii) Granulation Tissue Formation

Within 48 hours after a graft has been applied, fibroblasts begin to proliferate and migrate into the site of the graft from the connective tissue at the edge of the graft. It has surprisingly been found that application of the active enamel substance at the site of a graft stimulates the fibroblasts to produce collagens and glycosaminoglycans which participate in the attachment of the graft to the graft bed. Inter alia low oxygen tension at the graft stimulates proliferation of epithelial cells which give rise to the formation of a new capillary network. In accordance with the present invention, it has surprisingly been found that application of the active enamel substance to the recipient bed, preferably before application of the graft stimulates the proliferation of fibroblasts and their production of a number of growth factors, such as TGF-β, PDGF and interleukin-6. It is therefore concluded that the active enamel substance promotes the processes, in particular the formation of granulation tissue, that permit a graft to take, that is, attach firmly to the recipient bed. The active enamel substance may be applied for a period of up to 72 hours before the graft is applied on the recipient bed in order to ensure a desirable stimulation of fibroblasts to promote the take of the graft.

Collagenases and plasminogen activators are secreted from keratinocytes. If the graft is left undisturbed and well-nourished with oxygen and nutrients, keratinocytes will migrate into the graft bed. Keratinocytes are believed only to migrate over viable connective tissue and, accordingly, the keratinocytes migrate into the area below the dead tissue and the crust of the wound at the edges of the graft.

Clinical healing of the graft is said to have occurred when no tissue interruption can be visually observed and only discrete signs of inflammation are present such as a light redness, exudate or a discretely swollen tissue. In addition, no complaints of pain are present when the grafted tissue is relaxed or untouched.

As mentioned above, the invention relates to the use of enamel matrix, enamel matrix derivatives and/or enamel matrix proteins as an agent which accelerates, stimulates or promotes the take of a graft.

It has previously been suggested that growth factors like epidermal growth factor (EGF), transforming growth factor-α (TGF-α), platelet derived growth factor (PDGF), fibroblast growth factors (FGFs) including acidic fibroblast growth factor (α-FGF) and basic fibroblast growth factor (β-FGF), transforming growth factor-β (TGF-β) and insulin like growth factors (IGF-1 and IGF-2) are conductors of the wound healing process and they are frequently cited as promoters of wound healing, also in connection with grafting; however, they can actually lead to fibrosis which in turn can itself impair successful healing. Even though accelerated healing offers the most promise for reducing the risk of infection and the resulting inflammation that can result in scar formation, therapeutic attempts to accelerate the normal graft healing process have met with relatively little success. This is likely because the repair process involves the concerted involvement of a number of factors, cf. above.

To this end, the present inventors have observed that in various cell cultures of fibroblasts (embryonal, dermal, derived from the periodontal ligament, fish or bird), four times as much TGFβ1 is produced in the cell cultures stimulated with EMDOGAIN® compared to non-stimulated cultures when assayed by, e.g., ELISA in a sample from the culture medium. The increase is present after 24 hours of culture, but more significant on the following days (days 3 and 4). After the second day, also the cell proliferation is increased in cell cultures stimulated with EMDOGAIN®. As TGFβ1 seems to be of central importance in the epithelisation of skin and mucosal grafts, these findings support the concept of the present invention.

The present inventors have now found that enamel matrix, enamel matrix derivatives and/or enamel matrix proteins have graft healing properties. Furthermore, there are indications of that the application of enamel matrix, enamel matrix derivatives and/or enamel matrix proteins to sites of graft lead to improved attachment and/or healing. Especially, the inventors have observed that after application of enamel matrix proteins and/or enamel matrix derivatives, the inflammation stage is shortened and the typical signs such as warmth, redness, oedema and pain are less noticeable, and new tissues are formed more rapidly. The observed time for graft healing (e.g. after dermatological surgery) is substantially reduced as compared to surgery without the use of enamel matrix, enamel matrix derivatives and/or enamel matrix proteins.

An additional advantage in the use according to the invention of the active enamel substance is that it has been found to exhibit infection-decreasing properties. As infections are a frequent complication in connection with grafting which may result in graft rejection or, at the very least, in impaired healing of the graft and an increased risk of scarring, the infection-decreasing properties of the active enamel substance contribute to the improvements in attachment and healing of the graft observed when using the active enamel substance. In particular, the active enamel substance has been found to have antibacterial properties in the sense that it suppresses the growth of bacteria. Of particular interest for the present purpose is the inhibition of bacteria causing wound infections, in particular *Staphylococci* such as *Staphylococcus aureus*.

The therapeutic and/or prophylactic activity of the active enamel substance may of course be evidenced by in vivo tests using experimental animals (cf. Example 2 below) or humans. However, an indication of the efficacy and/or activity of the active enamel substance can be obtained by performing relatively simple in vitro tests such as, e.g., tests involving cell cultures.

Furthermore, there are several parameters which may be employed in order to evaluate a graft healing effect. These include:

Computer aided planimetry (evaluation of rate of graft healing)

Laser doppler imaging (evaluation of graft perfusion)

Tensiometry (evaluation of graft strength)

Histopathology/cytology (microscopic evaluation of graft tissues and fluids)

Biochemistry (HPLC/RIA/ELISA) (evaluation of various drugs and biochemical components of tissue healing)

Electrodiagnostics (evaluation of relationship of graft healing and innervation)

Scintigraphy (radionuclide imaging of graft tissue)

In connection with the preparation of sites for grafting, debridement and cleansing of the graft bed may be of particular importance. It is believed that the cleansing and/or debridement of graft beds before grafting are a prerequisite for the successful attachment of the graft and the graft healing process. It is further believed that the active enamel substance has to exert its effect on fresh and vital tissue and not on dead or contaminated tissue. Debridement of necrotic tissue may be carried out by at least four different methods: (1) sharp debridement, (2) mechanical debridement, (3) enzymatic debridement and (4) autolytic debridement.

Accordingly, in the use of the active enamel substance according to the present invention for preparation of graft beds containing necrotic tissue, a debridement method is suitably carried out before application of the active enamel substance and attachment of the graft.

Enamel Matrix, Enamel Matrix Derivatives and Enamel Matrix Proteins

Enamel matrix is an actodentally derived precursor to enamel and may be obtained from any relevant natural source, i.e. a mammal in which teeth are under development. A suitable source is developing teeth from slaughtered animals such as, e.g., calves, pigs or lambs. Another source is for example fish skin.

Enamel matrix can be prepared from developing teeth as described previously (EP-B-0 337 967 and EP-B-0 263 086). The enamel matrix is scraped off and enamel matrix derivatives are prepared, e.g. by extraction with aqueous solution such as a buffer, a dilute acid or base or a water/solvent mixture, followed by size exclusion, desalting or other purification steps, followed by freeze-drying. Enzymes may be deactivated by treatment with heat or solvents, in which case the derivatives may be stored in liquid form without freeze-drying.

In the present context, enamel matrix derivatives are derivatives of enamel matrix which include one or several of enamel matrix proteins or parts of such proteins, produced naturally by alternate splicing or processing, or by either enzymatic or chemical cleavage of a natural length protein, or by synthesis of polypeptides in vitro or in vivo (recombinant DNA methods or cultivation of diploid cells). Enamel matrix protein derivatives also include enamel matrix related polypeptides or proteins. The polypeptides or proteins may be bound to a suitable biodegradable carrier molecule, such as polyamino acids or polysaccharides, or combinations thereof. Furthermore, the term enamel matrix derivatives also encompasses synthetic analogous substances.

Proteins are biological macromolecules constituted by amino acid residues linked together by peptide bonds. Proteins, as linear polymers of amino acids, are also called polypeptides. Typically, proteins have 50–800 amino acid residues and hence have molecular weights in the range of from about 6,000 to about several hundred thousand Daltons or more. Small proteins are called peptides or oligopeptides.

Enamel matrix proteins are proteins which normally are present in enamel matrix, i.e. the precursor for enamel (Ten Cate: Oral Histology, 1994; Robinson: Eur. J. Oral Science, Jan. 1998, 106 Suppl. 1:282–91), or proteins which can be obtained by cleavage of such proteins. In general such proteins have a molecular weight below 120,000 daltons and include amelogenins, non-amelogenins, proline-rich non-amelogenins, amelins (amelo-blastin, sheathlin), enamelins and tuftelins.

Examples of proteins for use according to the invention are amelogenins, proline-rich non-amelogenins, tuftelin, tuft proteins, serum proteins, salivary proteins, amelin, amelo-blastin, enamelins, sheathlin, and derivatives thereof, and mixtures thereof. A preparation containing an active enamel substance for use according to the invention may also contain at least two of the aforementioned proteinaceous substances. Moreover, other proteins for use according to the invention are found in the marketed product EMDOGAIN® (Biora AB).

In general, the major proteins of an enamel matrix are known as amelogenins. They constitute about 90% w/w of the matrix proteins. The remaining 10% w/w includes proline-rich non-amelogenins, tuftelin, enamelins, tuft proteins, serum proteins and at least one salivary protein; however, other proteins may also be present such as, e.g., amelin (amelo-blastin, sheathlin) which have been identified in association with enamel matrix. Furthermore, the various proteins may be synthesized and/or processed in several different sizes (i.e. different molecular weights). Thus, the dominating proteins in enamel matrix, amelogenins, have been found to exist in several different sizes which together form supramolecular aggregates. They are markedly hydrophobic substances which under physiologically conditions form insoluble aggregates. They may carry or be carriers for other proteins or peptides.

Other protein substances are also contemplated to be suitable for use according to the present invention. Examples include proteins such as proline-rich proteins and poly-proline. Other examples of substances which are contemplated to be suitable for use according to the present invention are aggregates of such proteins, of enamel matrix derivatives and/or of enamel matrix proteins as well as metabolites of enamel matrix, enamel matrix derivatives and enamel matrix proteins. The metabolites may be of any size ranging from the size of proteins to that of short peptides.

As mentioned above, the proteins, polypeptides or peptides for use according to the invention typically have a molecular weight of at the most about 120 kDa such as, e.g., at the most 100 kDa, 90 kDa, 80 kDa, 70 kDa or 60 kDa as determined by SDS Page electrophoresis.

The proteins for use according to the invention are normally presented in the form of a preparation, wherein the protein content of the active enamel substance in the preparation is in a range of from about 0.05% w/w to 100% w/w such as, e.g., about 5–99% w/w, about 10–95% w/w, about 15–90% w/w, about 20–90% w/w, about 30–90% w/w, about 40–85% w/w, about 50–80% w/w, about 60–70% w/w, about 70–90% w/w, or about 80–90% w/w.

A preparation of an active enamel substance for use according to the invention may also contain a mixture of proteins with different molecular weights.

The proteins of an enamel matrix can be divided into a high molecular weight part and a low molecular weight part, and it has been found that a well-defined fraction of enamel matrix proteins possesses valuable properties with respect to treatment of periodontal defects (i.e. periodontal wounds). This fraction contains acetic acid extractable proteins generally referred to as amelogenins and constitutes the low molecular weight part of an enamel matrix (cf. EP-B-0 337 967 and EP-B-0 263 086).

As discussed above the low molecular weight part of an enamel matrix has a suitable activity for inducing binding between hard tissues in periodontal defects. In the present context, however, the active proteins are not restricted to the low molecular weight part of an enamel matrix. At present, preferred proteins include enamel matrix proteins such as amelogenin, amelin, tuftelin, etc. with molecular weights (as measured in vitro with SDS-PAGE) below about 60,000 daltons but proteins having a molecular weight above 60,000 daltons have also promising properties as candidates for wound healing, anti-bacterial and/or anti-inflammatory agents.

Accordingly, it is contemplated that the active enamel substance for use according to the invention has a molecular weight of up to about 40,000 such as, e.g. a molecular weight of between about 5,000 and about 25,000.

Within the scope of the present invention are also peptides as described in WO 97/02730, i.e. peptides which comprise at least one sequence element selected from the group consisting of the tetrapeptides DGEA (Asp-Gly-Glu-Ala), VTKG (Val-Thr-Lys-Gly), EKGE (Glu-Lys-Gly-Glu) and DKGE (Asp-Lys-Gly-Glu) and which further comprise an amino acid sequence from which a consecutive string of 20 amino acids is identical to a degree of at least 80% with a string of amino acids having the same length selected from the group consisting of the amino acid sequence shown in SEQ ID NO:1 and a sequence consisting of amino acids 1 to 103 of SEQ ID NO:1 and amino acids 6 to 324 of SEQ ID NO:2 shown in WO 97/02730.

By the term "sequence identity" is meant the identity in sequence of amino acids in the match with respect to identity and position of the amino acids of the peptides. A gap is counted as non-identity for one or more amino acids as appropriate.

Such peptides may comprise from 6 to 300 amino acids, e.g. at least 20 amino acids, at least 30 amino acids, such as at least 60 amino acids, at least 90 amino acids, at least 120 amino acids, at least 150 amino acids or at least 200 amino acids.

A method for the isolation of enamel matrix proteins involves extraction of the proteins and removal of calcium and phosphate ions from solubilized hydroxyapatite by a suitable method, e.g. gel filtration, dialysis or ultrafiltration (see e.g. Janson, J-C & Ryd én, L. (Eds.), Protein purification, VCH Publishers 1989 and Harris, ELV & Angal, S., Protein purification methods—A practical approach, IRL Press, Oxford 1990).

A typical lyophilized protein preparation may mainly or exclusively up to 70–90% contain amelogenins with a molecular weight (MW) between 40,000 and 5,000 daltons, the 10 –30% being made up of smaller peptides, salts and residual water. The main protein bands are at 20 kDa, 12–14 kDa and around 5 kDa.

By separating the proteins, e.g. by precipitation, ion-exchange chromatography, preparative electrophoresis, gel permeation chromatography, reversed phase chromatography or affinity chromatography, the different molecular weight amelogenins can be purified.

The combination of molecular weight amelogenins may be varied, from a dominating 20 kDa compound to an aggregate of amelogenins with many different molecular weights between 40 and 5 kDa, and to a dominating 5 kDa compound. Other enamel matrix proteins such as amelin, tuftelin or proteolytic enzymes normally found in enamel matrix, can be added and carried by the amelogenin aggregate.

As an alternative source of the enamel matrix derivatives or proteins one may also use generally applicable synthetic routes well-known for a person skilled in the art or use cultivated cells or bacteria modified by recombinant DNA techniques (see, e.g., Sambrook, J. et al.: Molecular Cloning, Cold Spring Harbor Laboratory Press, 1989).

Physico-Chemical Properties of Enamel Matrix, Enamel Matrix Derivatives and Enamel Matrix Proteins In general the enamel matrix, enamel matrix derivatives and enamel matrix proteins are hydrophobic substances, i.e. less soluble in water especially at increased temperatures. In general, these proteins are soluble at non-physiological pH values and at a low temperature such as about 4–20° C., while they will aggregate and precipitate at body temperature (35–37° C.) and neutral pH.

At least part of the active enamel substance for use according to the invention may be in the form of aggregates or after application in vivo is capable of forming aggregates. The particle size of the aggregates is in a range of from about 20 nm to about 1 μm.

It is contemplated that the solubility properties of the active enamel substance are of importance in connection with the prophylactic and therapeutic activity of the substance. When a composition containing the active enamel substance is administered to e.g. a human, the proteinaceous substances will precipitate due to the pH normally prevailing under physiological conditions. Thus, a layer of enamel matrix, enamel matrix derivatives and/or enamel matrix proteins is formed at the application site and this layer (which also may be a molecular layer in those cases where aggregates have been formed) is difficult to rinse off under physiological conditions. Furthermore, due to the substances bioadhesive properties (see below) the precipitated layer is firmly bound to the tissue also at the margin between the precipitated layer and the tissue. The proteinaceous layer thus covers the tissue onto which the active enamel substance or compositions thereof have been applied and the active enamel substances are maintained in situ for a prolonged period of time, i.e. it is not necessary to administer the active enamel substance with short intervals. Furthermore, the layer formed in situ can almost be compared to an occlusive dressing, i.e. the layer formed protects the tissue onto which the layer is formed from the surroundings. In the case of grafted tissue such a layer protects such tissue from further contamination from microorganisms present in the surroundings. Furthermore, the proteinaceous layer may exert its effect by direct contact with the tissue or with microorganisms present in/on/at the tissue.

In order to enable a proteinaceous layer to be formed in situ after application it may be advantageous to incorporate a suitable buffer substance in a pharmaceutical or cosmetic composition of the active enamel substance; the purpose of such a buffer substance could be to avoid the dissolution of the active enamel substance at the application site.

The active enamel substance have also been observed (by the present inventors) to posses bioadhesive properties, i.e. they have an ability to adhere to skin surfaces. These properties are most valuable in connection with a therapeutic and/or prophylactic treatment at least for the following reasons:

the prophylactically and/or therapeutically active substance(s) can be maintained at the application site for a prolonged period of time (i.e. i) the administration frequency can be reduced, ii) a controlled release effect of the active substance is obtainable and/or iii) a local treatment at the application site is improved)

the substances may in themselves be suitable as vehicles for other prophylactically or therapeutically active substances because a vehicle containing the active enamel substance can be formulated as a bioadhesive vehicle (i.e. a novel bioadhesive drug delivery system based on the bioadhesive properties of the active enamel substance.

Theories with Respect to Mechanism of Action

Enamel matrix is an example of an extracellular protein matrix which adheres to mineral surfaces as well as to proteinaceous surfaces. At physiological pH and temperature the proteins form an insoluble supra-molecular aggregate (Fincham et al. in J. Struct. Biol. 1994 March–April; 112(2):103–9 and in J. Struct. Biol. 1995 July–August; 115(1):50–9), which is gradually degraded by proteolytic enzymes (occurs both in vivo and in vitro provided that the proteases have not been subjected to inactivation).

In many species, remnants of enamel matrix are found in the newly mineralized crown when a tooth is erupting into the oral cavity. It might be argued that a new tooth would be very vulnerable to bacterial attack from common oral bacteria unless it had a natural protection during this initial phase. This is supported by the fact that children with amelogenesis imperfecta develop fewer caries lesions (cf. S. Sundell, Swed. Dent J. 10(4), 1986, pp. 151–163).

In accordance with the present invention, the active enamel substance may be used for curative purposes as well as for preventive purposes. Furthermore, the active enamel substance may be used together with other active drug substances such as, e.g. anti-bacterial, anti-inflammatory, antiviral, antifungal substances, immunosuppressive agents such as cyclosporins or ascomycins, or in combination with growth factors such as, e.g., TGFβ, PDGF, IGF, FGF, EGF, keratinocyte growth factor or peptide analogues thereof (it is believed that EGF promotes healing by enhancing migration and cell division of epithelial cells; furthermore, EGF increases fibroblast numbers in wounds resulting in a greater collagen production). Enzymes—either inherently present in the enamel matrix or preparation thereof or added—may also be used in combination with the active enamel substance, especially proteases.

A preparation of the active enamel substance is normally formulated as a pharmaceutical or cosmetic composition. Such a composition may of course consist of the proteinaceous preparation or it may further comprise a pharmaceutically acceptable excipient. Especially suitable excipients for use in pharmaceutical or cosmetic compositions are propylene gly-col alginate, or hyaluronic acid or salts or derivatives thereof.

Pharmaceutical or Cosmetic Compositions

In the following, examples of suitable compositions containing the active enamel sub-stance are given. Depending on the use of the active enamel substance, a composition may be a pharmaceutical or cosmetic composition. In the following, the term "pharmaceutical composition" is also intended to encompass cosmetic compositions as well as compositions belonging to the grey area between pharmaceuticals and cosmetics, the so-called cosmeceuticals.

For the administration to an individual (an animal or a human) the active enamel sub-stance and/or a preparation thereof are preferably formulated into a pharmaceutical composition containing the active enamel substance and, optionally, one or more pharmaceutically acceptable excipients.

The compositions may be in form of, e.g., solid, semi-solid or fluid compositions such as, e.g., bioabsorbable patches, drenches, dressings, hydrogel dressings, hydrocolloid dressings, films, foams, sheets, bandages, plasters, delivery devices, implants, powders, granules, granulates, capsules, agarose or chitosan beads, tablets, pills, pellets, microcapsules, microspheres, nanoparticles, gels, hydrogels, pastes, ointments, creams, soaps, solutions, dispersions, suspensions, emulsions, mixtures, lotions, kits containing e.g. two separate containers, wherein the first one of the containers contains the active enamel substance, e.g. in powder or freeze-dried form, optionally admixed with other active drug substance(s) and/or pharmaceutically acceptable excipients and the second container containing a suitable medium intended to be added to the first container before use in order to obtain a ready-to-use composition;

Compositions for application to the skin or to the mucosa are considered most important in connection with the present invention. Thus, a composition comprising the active enamel substance to be administered may be adapted for administration by any suitable route, for example by topical (dermal) administration. Furthermore, a composition may be adapted to administration in connection with surgery, e.g. in connection with incision within the body in order to promote healing internal tissue damage such as bone or cartilage grafts.

The compositions may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

A pharmaceutical composition comprising an active enamel substance serves as a drug delivery system. In the present context the term "drug delivery system" denotes a pharmaceutical composition (a pharmaceutical formulation or a dosage form) which upon ad-ministration presents the active substance to the body of a human or an animal. Thus, the term "drug delivery system" embraces plain pharmaceutical compositions such as, e.g., creams, ointments, liquids, powders, etc. as well as more sophisticated formulations such as sprays, plasters, bandages, dressings, devices, etc.

Apart from the active enamel substance, a pharmaceutical composition for use according to the invention may comprise pharmaceutically acceptable excipients.

A pharmaceutically acceptable excipient is a substance which is substantially harmless to the individual to which the composition is to be administered. Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

Whether a pharmaceutically acceptable excipient is suitable for use in a pharmaceutical composition is generally dependent on which kind of dosage form is chosen for use for a particular kind of wound. In the following are given examples of suitable pharmaceutically acceptable excipients for use in different kinds of compositions for use according to the invention.

In the following is given a review on relevant pharmaceutical compositions for use according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

The choice of pharmaceutically acceptable excipient(s) in a composition for use according to the invention and the optimum concentration thereof cannot generally be predicted and must be determined on the basis of an experimental evaluation of the final composition. However, a person skilled in the art of pharmaceutical formulation can find guidance in e.g., "Remington's Pharmaceutical Sciences", 18th Edition, Mack Publishing Company, Easton, 1990.

Topical Compositions

For application to the mucosa or the skin, the compositions for use according to the invention may contain conventionally non-toxic pharmaceutically or cosmetically acceptable carriers and excipients including microspheres and liposomes.

The compositions for use according to the invention include all kinds of solid, semi-solid and fluid compositions. Compositions of particular relevance are e.g. pastes, ointments, hydrophilic ointments, creams, gels, hydrogels, solutions, emulsions, suspensions, lotions, liniments, shampoos, jellies, soaps, sticks, sprays, powders, films, foams, pads, sponges (e.g. collagen sponges), pads, dressings (such as, e.g., absorbent wound dressings), drenches, bandages and plasters.

The pharmaceutically acceptable excipients may include solvents, buffering agents, preservatives, humectants, chelating agents, antioxidants, stabilizers, emulsifying agents, suspending agents, gel-forming agents, ointment bases, penetration enhancers, perfumes, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sun-flower oil, and teaseed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethylamine etc.

Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are glycerin, propylene glycol, sorbitol, lactic acid, urea, and mixtures thereof.

Examples of chelating agents are sodium EDTA and citric acid.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin; sorbitan monooleate derivatives; wool fats; wool alcohols; sorbitan esters; monoglycerides; fatty alcohols;, fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carraghenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol aginate.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes.

Examples of hydrophilic ointment bases are solid macrogols (polyethylene glycols).

Other examples of ointment bases are triethanolamine soaps, sulphated fatty alcohol and polysorbates.

Examples of powder components are: alginate, collagen, lactose, powder which is able to form a gel when applied to a graft (absorbs liquid/wound exudate). Normally, powders intended for application on grafts must be sterile and the particles present must be micronized.

Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and chitosans.

Dressings and/or bandages may also be used as delivery systems for the active enamel substance. When dressings are used as dosage form, the active enamel substance may be admixed with the other ingredients before or during the manufacture of the dressing or, the active enamel substance may in some way be coated onto the dressing e.g. by dip-ping the dressing in a solution or dispersion of the active enamel substance or by spraying a solution or dispersion of the active enamel substance onto the dressing. Alternatively, the active enamel substance may be applied in the form of a powder to the dressing. Dressings may be in the form of absorbent wound dressings for application to exuding wounds. Dressings may also be in the form of hydrogel dressings (e.g. cross-linked polymers such as, e.g. Intrasite® which contains carboxymethylcellulose, propylene glycol or polysaccharide, disaccharide and proteins) or in the form of occlusive dressings such as, e.g., alginates, chitosan, hydrophilic polyurethane film, collagen sheets, plates, powders foams, or sponges, foams (e.g. polyurethane or silicone), hydrocolloids (e.g. carboxymethylcellulose, CMC), collagen and hyaluronic acid-based dressings including combinations thereof.

Alginate, chitosan and hydrocolloid dressings take up wound exudate when placed on a graft. When doing so they produce an aqueous gel on the surface of the graft and this gel is believed to be beneficial for the healing of the graft due to the retention of moisture at the site of the graft.

Compositions which have proved to be of importance in connection with topical application are those which have thixotropic properties, i.e. the viscosity of the composition is affected e.g. by shaking or stirring so that the viscosity of the composition at the time of ad-ministration can be reduced and when the composition has been applied, the viscosity increases so that the composition remains at the application site.

Dosages of Enamel Matrix, Enamel Matrix Derivatives and Enamel Matrix Proteins

In a pharmaceutical composition for use according to the invention on skin or mucosa, an active enamel substance is generally present in a concentration ranging from about 0.01% to about 99.9% w/w. The amount of composition applied will normally result in an amount of total protein per $cm^2$ area of the recipient bed corresponding to from about 0.01 $mg/cm^2$ to about 20 $mg/cm^2$ such as from about 0.1 $mg/cm^2$ to about 15 $mg/cm^2$.

The amount applied of the composition depends on the concentration of the active enamel substance in the composition and of the release rate of the active enamel sub-stance from the composition, but is generally in a range corresponding to at the most about 15–20 $mg/cm^2$.

In those cases where the active enamel substance is administered in the form of a liquid composition, the concentration of the active enamel substance in the composition is in a range corresponding to from about 0.1 to about 50 mg/ml. Higher concentrations are in some cases desirable and can also be obtained such as a concentration of at least about 100 mg/ml.

The concentration of the active enamel substance in a pharmaceutical composition depends on the specific enamel substance, its potency, the severity of the disease to be prevented or treated, and the age and condition of the patient. Methods applicable to selecting relevant concentrations of the active enamel substance in the pharmaceutical composition are well known to a person skilled in the art and may be performed according to established guidelines for good clinical practice (GCP) or Investigational New Drug Exemption ("IND") regulations as described in e.g. International Standard ISO/DIS 14155 Clinical investigation of medical devices, 1994 and ICH (International Committee for Harmonisation): Harmonised tripartite guideline for good clinical practice, Brookwood Medical Publications, Ltd, Surrey, UK, 1996. A person skilled in the art would, by use of the methods described in standard textbooks, guidelines and regulations as described above as well as common general knowledge within the field, be able to select the exact dosage regimen to be implemented for any active enamel substance and/or selected other active substances and dosage form using merely routine experimentation procedures.

BRIEF DESCRIPTION OF THE DRAWINGS

The invention is further described in the following with reference to the appended drawings, wherein.

The present invention is further described in the following examples which are not in any way intended to limit the scope of the invention as claimed.

Experimental Section

Materials and Methods

Enamel Matrix Derivative, EMDOGAIN®, from BIORA AB, S-205 12 Malmö, Sweden containing 30 mg freeze-dried enamel matrix protein (in the following abbreviated EMD) and 1 ml vehicle solution (Propylene Glycol Alginate), which are mixed prior to application, unless the protein and the vehicle are tested separately. The weight ratio is about 85/5/10 between the main protein peaks at 20, 14 and 5 kDa, respectively.

EXAMPLES

Example 1

Materials and Methods

Normal human dermal fibroblasts were obtained from BioWhittaker, CC-2511, NHDF, single donor, adult male, Batch No. NHDF-4196, Lot No. 16503. The cells were grown in Dulbecco's Modified Eagle's Medium supplemented with 10% fetal calf serum. EMD was supplied both by surface coating culture dishes with a 0.5 mg/ml EMD solution in 0.1% HAc and by supplementing the medium with 100 μg EMD per ml medium. All experiments started at a cell density of 50,000 cells per ml culture medium.

Figure 1:
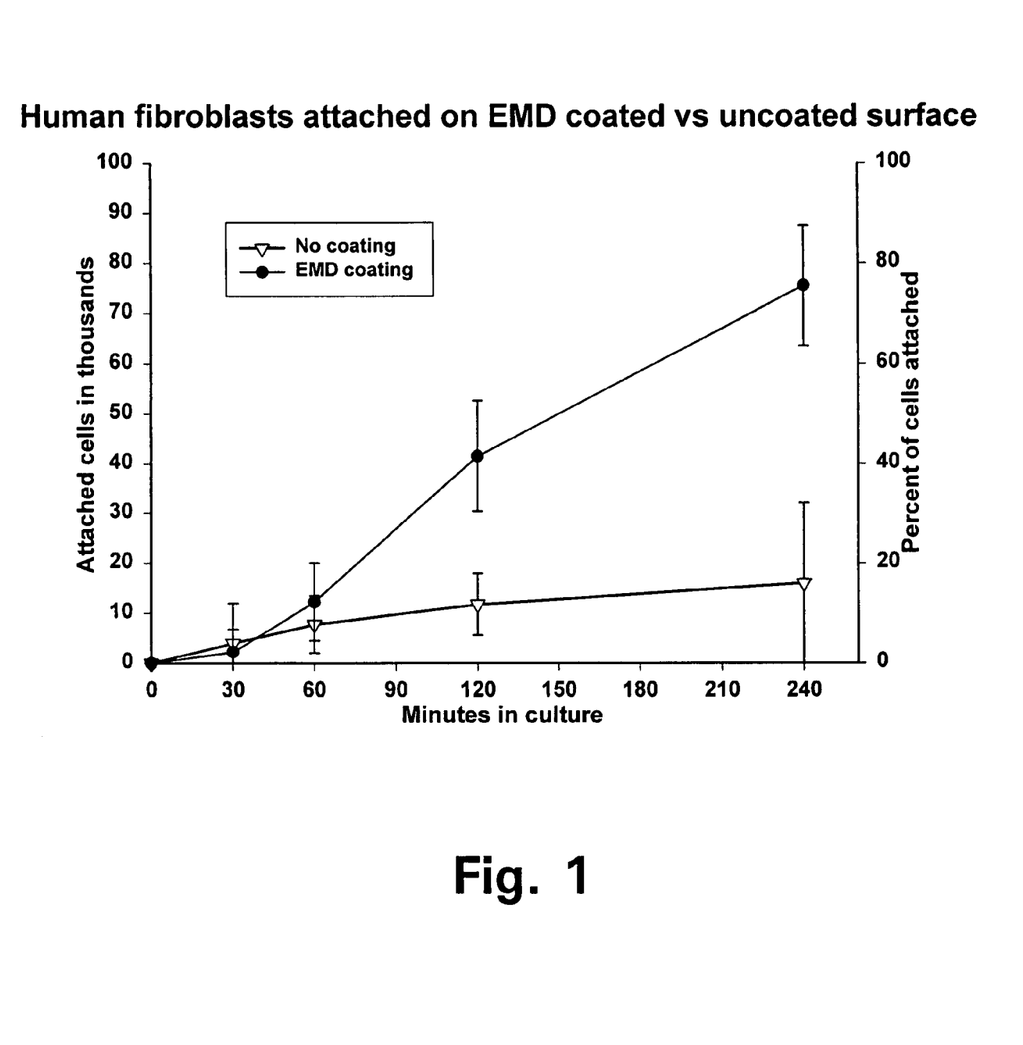
FIG. 1 is a graph showing the attachment of human dermal fibroblast (NHDF) cells to the surface of culture dishes coated with EMD compared to uncoated culture dishes used as controls.

(a) NHDF cells were grown on the surface of culture dishes coated with EMD for 30, 60, 120 or 240 min. before cultures were washed with PBS (phosphate buffered saline) to remove unattached cells. Cells grown in uncoated culture dishes served as controls. The attached cells were then loosened by trypsinisation and counted in a Bürker chamber (n=3 at each timepoint). It appears from FIG. 1 that initial attachment of NHDF cells is significantly increased by the presence of EMD.

Figure 2:
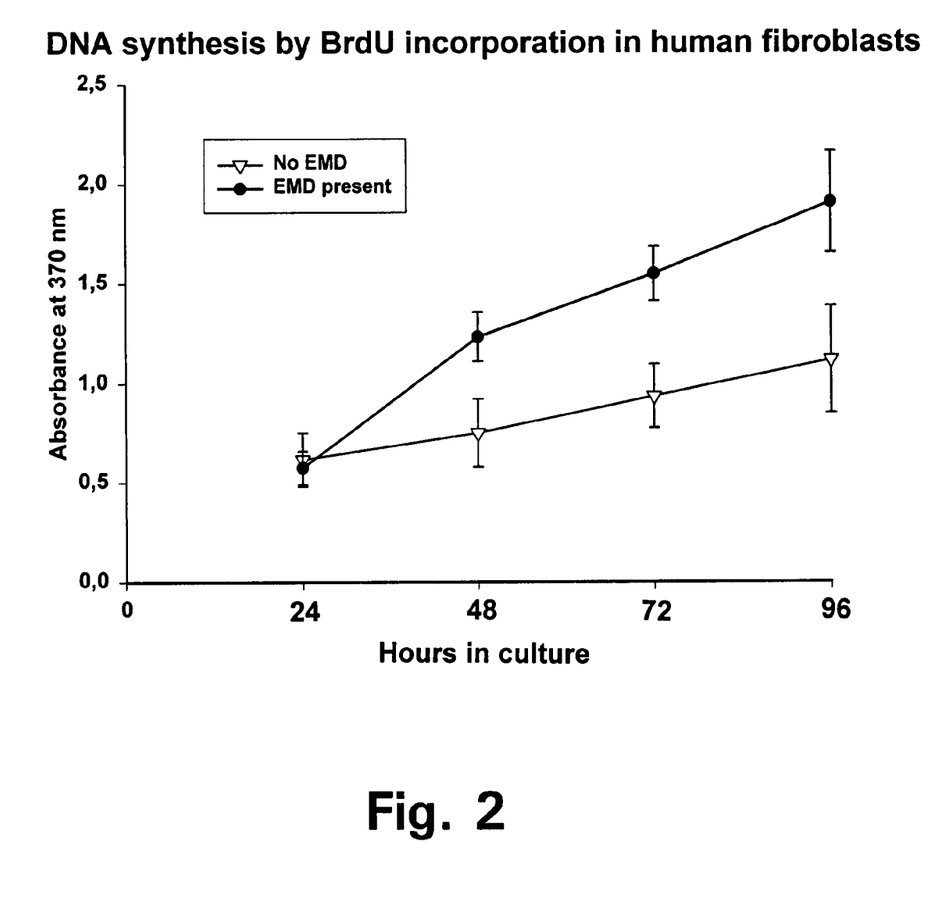
FIG. 2 is a graph showing DNA synthesis by NHDF cells grown in the presence or absence of EMD measured by incorporation of 5-bromo-2'-deoxyuridine (BrdU) into newly synthesised DNA of proliferating cells.

(b) NHDF cells were cultured for 24, 48, 72 or 96 hours in the presence or absence (controls) of EMD before they were subjected to a cell proliferation immunoassay measuring incorporation of 5-bromo-2'-deoxyuridine (BrdU). Over a period of 4 hours, BrdU was incorporated instead of thymidine into the newly synthesized DNA of proliferating cells. After labelling the cells were washed, fixed and denatured, and the amount of incorporated BrdU was measured by colorimetric ELISA using an anti-BrdU peroxidase-conjugated antibody in accordance with the manufacturer's instructions (Boehringer Mannheim, Cat. No. 1647 229) (n=6 at each timepoint). It appears from FIG. 2 that the cells grown in the presence of EMD exhibited an increase in DNA synthesis compared to control cells except at 24 hours.

Figure 3:
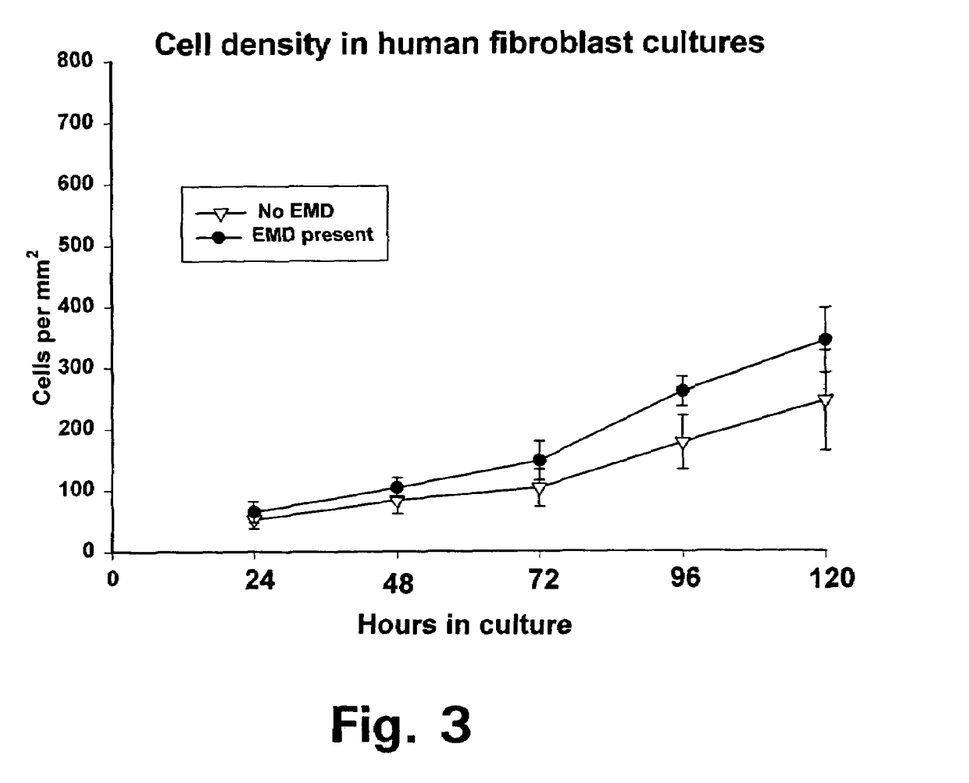
FIG. 3 is a graph showing the density after 72 hours of NHDF cells grown in the presence or absence of EMD.

(c) NHDF cells were grown in cultures for 24, 48, 72, 96 or 120 hours in the presence or absence (controls) of EMD. Cultures were then washed with PBS, and cells were counted in the microscope using a fixed grid. Five different areas were counted in each of six parallel cultures at each timepoint. At 72 hours, the cell cultures grown in the presence of EMD showed a rapid increase in cell density compared to untreated controls (FIG. 3).

Figure 4:
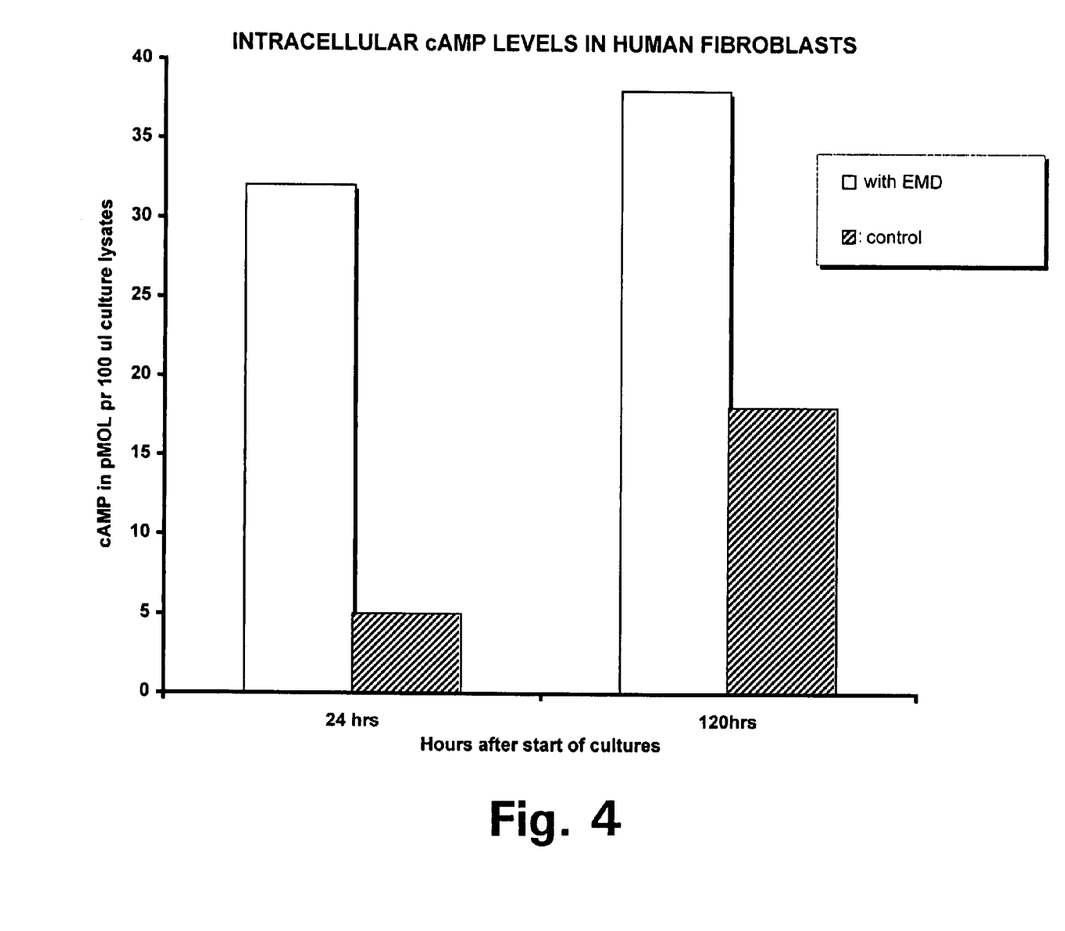
FIG. 4 is a graph showing the amount of intracellular cAMP in NHDF cells grown in the presence or absence of EMD.

(d) NHDF cells were cultured for 24 or 120 hours, washed twice with PBS and centrifuged. 100 μl of cells from each culture (n=6 at each timepoint/experiment) were then lysed, and released intracellular cAMP was measured by competitive enzyme immunoassay (EIA) using an Amersham Pharmacia Biotech "Biotrak cAMP EIA" kit (Cat. No. RPN 225) in accordance with the manufacturer's instructions. Compared to controls grown in the absence of EMD, NHDF cells show a marked increase in intracellular cAMP after 24 hours of growth in the presence of EMD (FIG. 4). This increase could still be observed after 120 hours in culture. The increase in intracellular cAMP suggests that cells grown in the presence of EMD generate internal signal(s) that could be part of pathways for growth regulation and differentiation.

Figure 5:
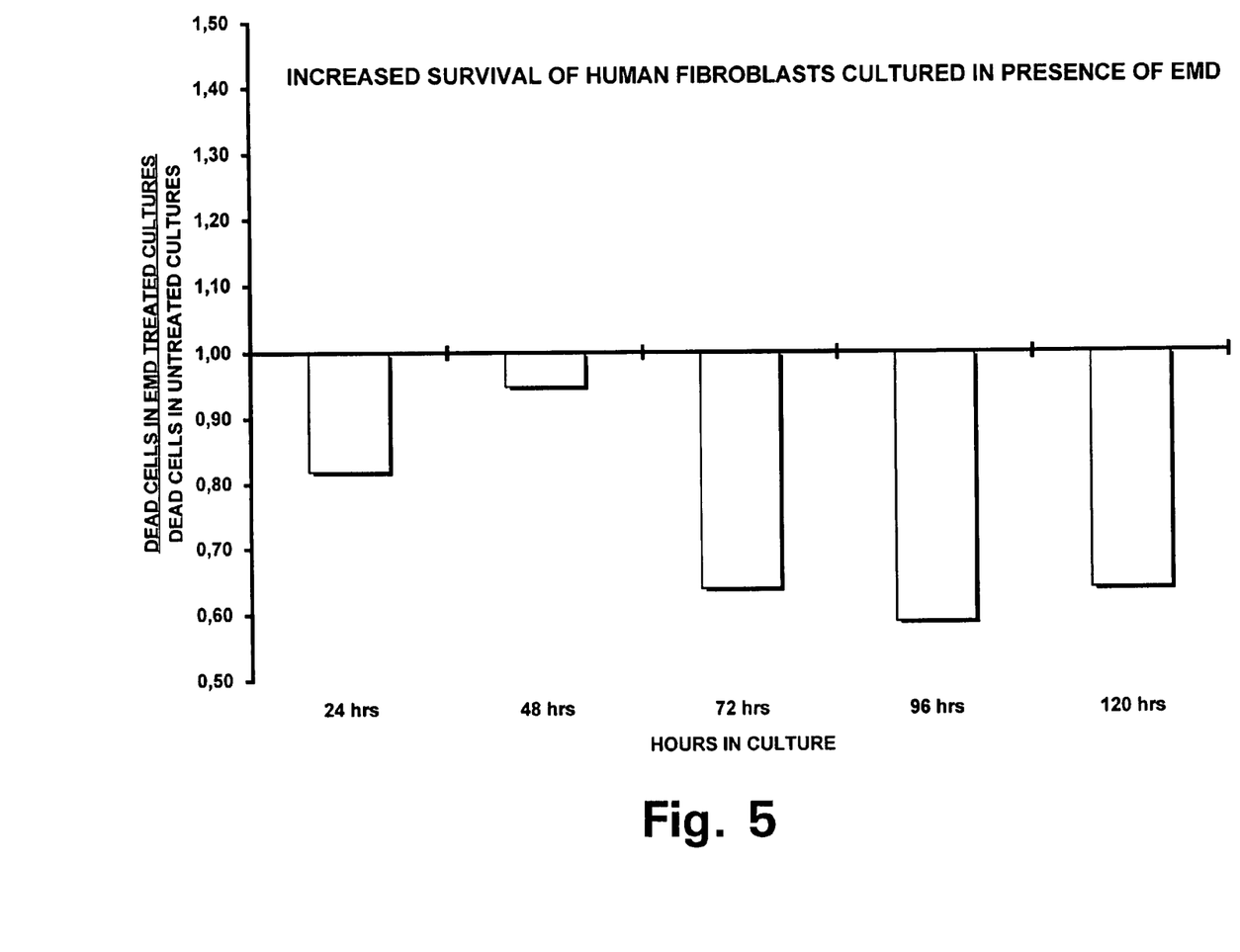
FIG. 5 is a graph showing the survival rate of NHDF cells grown in the presence or absence of EMD measured by the level of apoptosis specific nucleic acid degradation products.

(e) NHDF cells were harvested from cultures at 24, 48, 72, 96 or 120 hours (n=5 at each timepoint/experiment), washed in PBS and centrifuged. 200 μl of cells were lysed, and the level of apoptosis specific nucleic acid degradation products (histone associated DNA fragments) was quantified by sandwich ELISA using a Boehringer Mannheim "Cell Death Detection ELISA" kit (Cat. No. 1 774 425) according to the manufacturer's instructions. The results are presented as the ratio between EMD treated cells and untreated cells. Hence values above 1 indicate induced cell death while values below 1 reflect prolonged cell survival. It appears from FIG. 5 that the NHDF cells showed an increased survival rate when EMD is present in the cultures (values below 1).

Figure 6:
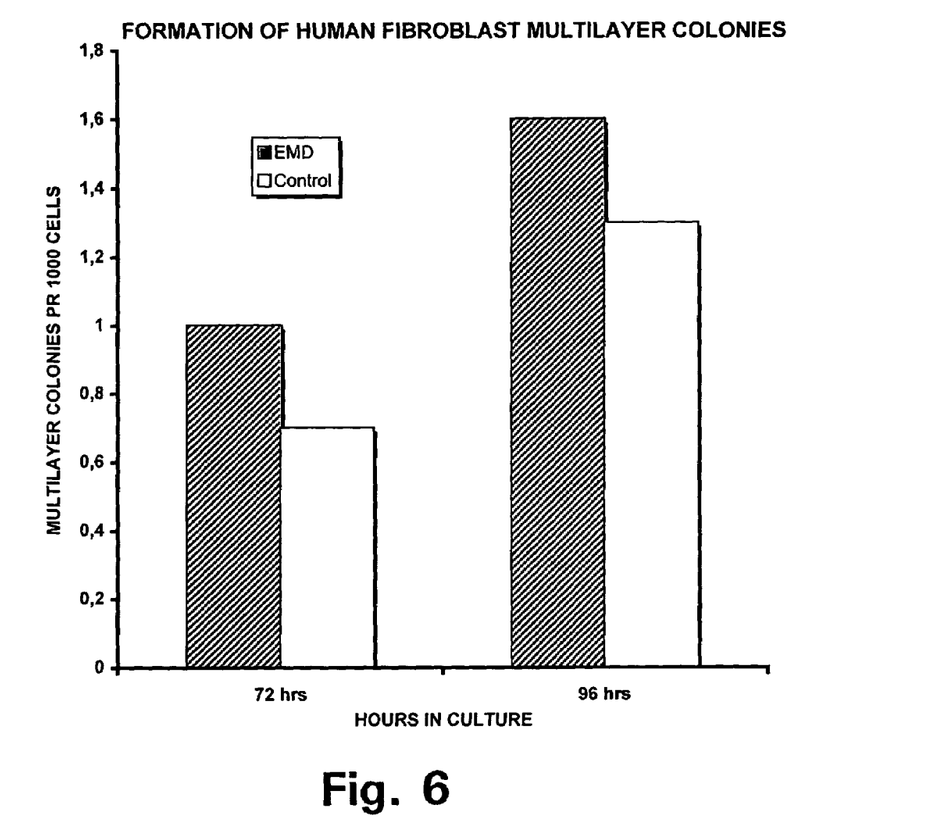
FIG. 6 is a graph showing the formation of multilayer colonies of NHDF cells after 72 and 96 hours in the presence or absence of EMD.

(f) NHDF cells were cultured for 24, 48, 72 or 96 hours in the presence or absence (controls) of EMD, washed with PBS, and the number of multilayer colonies was counted in the microscope using a fixed grid. Five different areas were counted in each of nine parallel cultures at each timepoint. The cells were then harvested by trypsinisation, counted in a Bürker chamber and the number of multilayer colonies per 1000 cells was calculated. It appears from FIG. 6 that the number of multilayer colonies in NHDF cell cultures increased when the cells were grown in the presence of EMD. Multilayer colony formation could be observed after 72 hours of culture and was preceded by an increase in cAMP (FIG. 4) and coincides with the onset of TGF-β production (not shown).

Based on these results, it was concluded that NHDF cells cultured in the presence of EMD exhibited faster replication, higher metabolic activity, increased attachment rate and development of a higher number of multilayer colonies.

Example 2

Pilot Skin Grafting Study in Pigs

Introduction

Objective

The objective of this pilot study was to evaluate the healing process of grafted split-thickness wounds in pigs, and to evaluate the effect of EMD on these wounds.

Materials and Methods

Animals

The experiment was performed in 4 female SPF pigs (crossbreed of Danish country, Yorkshire and Duroc). At start of the acclimatisation period the body weight of the animals was about 35 kg.

An acclimatisation period of one week was allowed during which the animals were observed daily in order to reject an animal presenting a poor condition. All observations were recorded.

Housing

The study took place in an animal room provided with filtered air at a temperature of 21° C.±3° C., relative humidity of 55%±15% and air change 10 times/hour. The room was illuminated to give a cycle of 12 hours light and 12 hours darkness. The animals were housed individually in pens.

Bedding

The bedding was softwood sawdust "LIGNOCEL H ¾" from Hahn & Co, D-24796 Bredenbek-Kronsburg. Regular analyses for relevant possible contaminants were performed.

Diet

A commercially available pig diet, "Altromin 9033" from Chr. Petersen A/S, DK4100 Ringsted was offered (about 800 g twice daily). Analyses for major nutritive components and relevant possible contaminants were performed regularly.

Drinking Water

Twice daily the animals were offered domestic quality drinking water. Analyses for relevant possible contaminants were performed regularly.

Wounding and Grafting

The wounds were established on day 1. The animals were anaesthetised with Stresnil® Vet. Janssen, Belgium (40 mg azaperone/ml, 1 ml/10 kg), and Atropin DAK, Denmark (1 mg atropine/ml, 0.5 ml/10 kg), given as a single intramuscular injection followed by i.v. injection of Hypnodil® Janssen, Belgium (50 mg metomidate/ml, about 2 ml).

An area dorso-laterally on either side of the back of the animal was shaved, washed with soap and water, disinfected with 70% ethanol which was rinsed off with sterile saline, and finally dried with sterile gauze.

Eight split-thickness wounds (25×25×0.4 mm) were made on the prepared area, 4 on each side of the spine, using an ACCU-Dermatom (GA 630, Aesculap®). The wounds were numbered 1 (most cranial) to 4 (most caudal) on the left side on the animal, and 5 (most cranial) to 8 (most caudal) on the right side of the animal. Just after wounding and hemostasis, the excised epidermis of the wounds of treatment C and D was replaced on the wound surface. Coagulated blood was removed with sterile gauze.

Just before surgery, about 8 hours after termination of surgery, and whenever necessary thereafter the animals were given an intramuscular injection of Anorfin®, A/S GEA, Denmark (0.3 mg buprenorphine/ml, 0.04 ml/kg).

Dosing

After wounding the graft beds were treated as follows:

| Localisation | Animal No. 1 | | Animal No. 2 | | Animal No. 3 | | Animal No. 4 | |
|---|---|---|---|---|---|---|---|---|
| | Left | Right | Left | Right | Left | Right | Left | Right |
| Cranial | | D | C | | | D | C | |
| | | | D | C | | | D | C |
| | C | | | C | D | | | D |
| Caudal | D | C | | | D | C | | |

C = Graft
D = Graft + EMD

At about 15 minutes before dosing, the EMD formulation was prepared according to the instructions given by the manufacturer. The EMD formulation was used within 2 hours after preparation. For the wounds of treatment D, EMD was applied as a thin layer between the replaced excised epidermis and the wound surface. One vial of EMD was used per 4 wounds.

Dressing

The wounds were dressed with Tegaderm®. The dressings were covered with a gauze bandage fixed by Fixomul®. The dressings, the gauze and the Fixomul® were retained by a netlike body-stocking. Bend-a-rete® (Tesval, Italy), The dressings were observed on a daily basis. The dressings were changed on day 2 (all animals) and 3 (animal Nos. 3 and 4).

Prior to each changing the animals were anaesthetised with an intramuscular injection in the neck (1.0 ml/10 kg body weight) of a mixture of Zoletil 50®Vet., Virbac, France (125 mg tiletamine and 125 mg zolazepam in 5 ml solvent, 5 ml) Rompun®Vet., Bayer, Germany (20 mg xylazine/ml, 6.5 ml) and Methadon® DAK, Nycomed DAK, Denmark (10 mg methadon/ml, 2.5 ml).

Observation of Grafts

Each graft was observed and photographed on day 2 (all animals), 3 (all animals) and 4 (animal Nos. 3 and 4). The degree of exudation and inflammation was evaluated.

Clinical Signs

All visible signs of ill health and any behavioural changes were recorded daily. Any deviation from normal was recorded with respect to time of onset, duration and intensity.

Body Weight

The animals were weighed on arrival, on the day of wounding and at termination of the study.

Terminal Observations

On day 3 (about 56 hours after wounding), animal Nos. 1 and 2 were killed by a cut on the subclavian vein and artery after stunning with a bolt pistol.

On day 4 (about 72 hours after wounding), animal Nos. 3 and 4 were killed by a cut on the subclavian vein and artery after stunning with a bolt pistol.

Tissue Sampling

Each wound was cut free as a block separated from skeletal muscle tissue. Each block was fixed in phosphate buffered neutral 4% formaldehyde.

Histological Preparation

After fixation four representative samples from all wounds were embedded in paraffin, cut at a nominal thickness of 5 µm and stained with haematoxylin and eosin. After staining the slides were observed under the light microscope using a grid. This allowed for measure-ments of the total length of the graft bed and length of the epithelialised surface. This ratio was expressed in percentage of graft bed covered by epithelial cells per slide. The mean values from each wound were taken, after which the group mean values were calculated.

Statistics

Data will be processed to give group mean values and standard deviations where appropriate. Possible outliers will be identified, too. Thereafter each continuous variable will be tested for homogeneity of variance with Bartlett's test. If the variance is homogeneous, analysis of variance will be carried out for the variable. If any significant differences are detected, possible intergroup differences will be assessed with Dunnett's test. If the variance is heterogeneous, each variable will be tested for normality by the Shapiro-Wilk method. In case of normal distribution, possible intergroup differences will be identified with Student's t-test, Otherwise the possible intergroup differences will be assessed by Kruskal-Wallis's test. If any significant intergroup differences are detected, the subsequent identification of the groups will be carried out with Wilcoxon Rank-Surn test.

The statistical analyses will be made with SAS® procedures (version 6.12) described in "SAS/STAT® User's Guide, Version 6, Fourth Edition, Vol. 1+2", 1989, SAS Institute Inc., Cary, N.C. 27513, USA.

Results

Clinical observations in the pilot study show rapid epithelialization of the grafted wounds which had been treated with EMD compared with untreated controls. Also, less exudate from the grafts was observed. The results from histology showed less exudate and fewer extravased blood cells, indicating less inflammation.

What is claimed is:

1. A method for providing for the take of a graft to a mammal in need thereof, the method comprising:
   a) providing the graft from one or more of the group consisting of a suitable donor, cultured epidermal cells, acellular dermal matrix, cellular matrix, skin and mucosa,
   b) applying a a prophylactically effective amount of an active enamel substance to a non-mineralized tissue recipient bed or lesion, and
   c) placing the graft on the non-mineralized tissue recipient bed or lesion.

2. A method according to claim 1, wherein the active enamel substance is applied in an amount of total protein per cm of graft bed area corresponding to from about 0.1 mg/cm$^2$ to about 15 mg/cm$^2$.

3. A method according to claim 1, wherein the active enamel substance is applied on the recipient bed or lesion before application of the graft described in step c.

4. A method according to claim 3, wherein the active enamel substance is applied for a period of up to 72 hours before the application of the graft.

5. A method according to claim 1, wherein the graft is a skin graft or mucosal graft.

6. A method according to claim 1, wherein the graft is an autogenous skin graft.

7. A method according to claim 1, wherein the graft is a full-thickness, split-thickness, composite, seed or mesh graft.

8. A method according to claim 1, wherein the graft comprises cultured epidermal cells.

9. A method according to claim 1, wherein the active enamel substance is enamel matrix, enamel matrix proteins, derivatives thereof, or mixtures thereof.

10. A method according to claim 1, wherein the active enamel substance is selected from the group consisting of enamelins, amelogenins, non-amelogenins, proline-rich amelogenins, amelins, tuftelins, mixtures thereof, and derivatives of said substances.

11. A method according to claim 1, wherein the active enamel substance has a molecular weight of up to about 120 kDa as determined by SDS Page electrophoresis.

12. A method according to claim 1, wherein the active enamel substance has a molecular weight of up to about 100 kDa as determined by SDS Page electrophoresis.

13. A method according to claim 1, wherein the active enamel substance has a molecular weight of up to about 60 kDa as determined by SDS Page electrophoresis.

14. A method according to claim 1, wherein the active enamel substance contains a mixture of active enamel substances with different molecular weights.

15. A method according to claim 1, wherein the preparation of an active enamel substance comprises at least one substance selected from the group consisting of amelogenins, proline-rich non-amelogenins, tuftelins, tuft proteins, serum proteins, salivary proteins, amelin, ameloblastin, sheathlin, mixtures thereof, and derivatives thereof.

16. A method according to claim 1, wherein the active enamel substance has a molecular weight of between about 5,000 and about 25,000.

17. A method according to claim 1, wherein the major part of the active enamel substance has a molecular weight of about 20 kDa.

18. A method according to claim 1, wherein at least a part of the active enamel substance is in the form of aggregates or after application in vivo is capable of forming aggregates.

19. A method according to claim 18, wherein the aggregates have a particle size of from about 20 nm to about 1 μm.

20. A method according to claim 1, wherein the protein content of the active enamel substance in the preparation is in a range of from about 0.05% w/w to 100% w/w.

21. A method according to claim 1, wherein the protein content of the active enamel substance in the preparation is in a range of from about 30–90% w/w.

22. A method according to claim 1, wherein a pharmaceutical or cosmetic composition comprising an active enamel substance and a pharmaceutically acceptable excipient is in step b) administered to the mammalian recipient bed or lesion.

23. A method according to claim 22, wherein the pharmaceutically acceptable excipient is propylene glycol alginate.

* * * * *

SEQUENCE LISTING

<160> NUMBER OF SEQ ID NOS: 5

<210> SEQ ID NO 1
<211> LENGTH: 407
<212> TYPE: PRT
<213> ORGANISM: rat

<400> SEQUENCE: 1

```
Met Ser Ala Ser Lys Ile Pro Leu Phe Lys Met Lys Gly Leu Leu Leu
 1               5                  10                  15

Phe Leu Ser Leu Val Lys Met Ser Leu Ala Val Pro Ala Phe Pro Gln
             20                  25                  30

Gln Pro Gly Ala Gln Gly Met Ala Pro Pro Gly Met Ala Ser Leu Ser
         35                  40                  45

Leu Glu Thr Met Arg Gln Leu Gly Ser Leu Gln Gly Leu Asn Ala Leu
     50                  55                  60

Ser Gln Tyr Ser Arg Leu Gly Phe Gly Lys Ala Leu Asn Ser Leu Trp
 65                  70                  75                  80

Leu His Gly Leu Leu Pro Pro His Asn Ser Phe Pro Trp Ile Gly Pro
                 85                  90                  95

Arg Glu His Glu Thr Gln Gln Pro Ser Leu Gln Pro His Gln Pro Gly
                100                 105                 110

Leu Lys Pro Phe Leu Gln Pro Thr Ala Ala Thr Gly Val Gln Val Thr
            115                 120                 125

Pro Gln Lys Pro Gly Pro His Pro Pro Met His Pro Gly Gln Leu Pro
        130                 135                 140

Leu Gln Glu Gly Glu Leu Ile Ala Pro Asp Glu Pro Gln Val Ala Pro
145                 150                 155                 160

Ser Glu Asn Pro Pro Thr Pro Glu Val Pro Ile Met Asp Phe Ala Asp
                165                 170                 175

Pro Gln Phe Pro Thr Val Phe Gln Ile Ala His Ser Leu Ser Arg Gly
            180                 185                 190

Pro Met Ala His Asn Lys Val Pro Thr Phe Tyr Pro Gly Met Phe Tyr
        195                 200                 205

Met Ser Tyr Gly Ala Asn Gln Leu Asn Ala Pro Gly Arg Ile Gly Phe
    210                 215                 220

Met Ser Ser Glu Glu Met Pro Gly Glu Arg Gly Ser Pro Met Ala Tyr
225                 230                 235                 240
```

-continued

```
Gly Thr Leu Phe Pro Gly Tyr Gly Phe Arg Gln Thr Leu Arg Gly
                245                 250                 255

Leu Asn Gln Asn Ser Pro Lys Gly Gly Asp Phe Thr Val Glu Val Asp
            260                 265                 270

Ser Pro Val Ser Val Thr Lys Gly Pro Glu Lys Gly Glu Gly Pro Glu
        275                 280                 285

Gly Ser Pro Leu Gln Glu Ala Ser Pro Asp Lys Gly Glu Asn Pro Ala
    290                 295                 300

Leu Leu Ser Gln Ile Ala Pro Gly Ala His Ala Gly Leu Leu Ala Phe
305                 310                 315                 320

Pro Asn Asp His Ile Pro Asn Met Ala Arg Gly Pro Ala Gly Gln Arg
                325                 330                 335

Leu Leu Gly Val Thr Pro Ala Ala Asp Pro Leu Ile Thr Pro Glu
                340                 345                 350

Leu Ala Glu Val Tyr Glu Thr Tyr Gly Ala Asp Val Thr Thr Pro Leu
                355                 360                 365

Gly Asp Gly Glu Ala Thr Met Asp Ile Thr Met Ser Pro Asp Thr Gln
            370                 375                 380

Gln Pro Pro Met Pro Gly Asn Lys Val His Gln Pro Gln Val His Asn
385                 390                 395                 400

Ala Trp Arg Phe Gln Glu Pro
                405
```

```
<210> SEQ ID NO 2
<211> LENGTH: 4
<212> TYPE: PRT
<213> ORGANISM: rat
<220> FEATURE:
<221> NAME/KEY: PEPTIDE
<222> LOCATION: (1)...(4)
<223> OTHER INFORMATION: DGEA

<400> SEQUENCE: 2

Asp Gly Glu Ala
1

<210> SEQ ID NO 3
<211> LENGTH: 4
<212> TYPE: PRT
<213> ORGANISM: rat
<220> FEATURE:
<221> NAME/KEY: PEPTIDE
<222> LOCATION: (1)...(4)
<223> OTHER INFORMATION: VTKG

<400> SEQUENCE: 3

Val Thr Lys Gly
1

<210> SEQ ID NO 4
<211> LENGTH: 4
<212> TYPE: PRT
<213> ORGANISM: rat
<220> FEATURE:
<221> NAME/KEY: PEPTIDE
<222> LOCATION: (1)...(4)
<223> OTHER INFORMATION: EKGE

<400> SEQUENCE: 4

Glu Lys Gly Glu
1
```

```
<210> SEQ ID NO 5
<211> LENGTH: 4
<212> TYPE: PRT
<213> ORGANISM: rat
<220> FEATURE:
<221> NAME/KEY: PEPTIDE
<222> LOCATION: (1)...(4)
<223> OTHER INFORMATION: DKGE

<400> SEQUENCE: 5

Asp Lys Gly Glu
 1
```